United States Patent [19]

Panster et al.

[11] Patent Number: 4,647,682
[45] Date of Patent: Mar. 3, 1987

[54] PHENYLENE GROUP-CONTAINING ORGANOSILANES AND PROCESSES FOR THE PREPARATION THEREOF

[75] Inventors: Peter Panster, Rodenbach; Peter Kleinschmit, Hanau, both of Fed. Rep. of Germany

[73] Assignee: Degussa Aktiengesellschaft, Frankfurt, Fed. Rep. of Germany

[21] Appl. No.: 865,486

[22] Filed: May 21, 1986

[30] Foreign Application Priority Data

May 25, 1985 [DE] Fed. Rep. of Germany ....... 3518878

[51] Int. Cl.$^4$ .............................. C07F 7/08; C07F 7/18
[52] U.S. Cl. .................................................... 556/431
[58] Field of Search ........................................ 556/431

[56] References Cited

U.S. PATENT DOCUMENTS 3,187,031  6/1965  Weyenberg ........................ 556/431
3,209,018  9/1965  Merker ........................... 556/431 X
3,387,015  6/1968  Piccoli ............................ 556/431

Primary Examiner—Paul F. Shaver
Attorney, Agent, or Firm—Beveridge, DeGrandi & Weilacher

[57] ABSTRACT

Phenylene group-containing organosilanes represented by the formula:

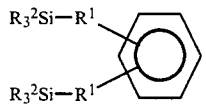

(1)

where in each case all three possible isomers in relation to the position of the $R_3Si-R^1$ substituents can be present concurrently, $R^1$ represents $-CH_2-CH_2-$ or $CH_3CH<$, and $R^2$ represents chloride or an alkoxy group. Processes for the production of the organosilanes and the use of these substances for the production of the corresponding organopolysiloxanes are also disclosed.

9 Claims, No Drawings

PHENYLENE GROUP-CONTAINING ORGANOSILANES AND PROCESSES FOR THE PREPARATION THEREOF

The invention relates to new phenylene group-containing organosilanes, which are of significance as monomeric precursors for corresponding organopolysiloxanes and other secondary polymer products, as well as to processes for the preparation of these new products.

Organopolysiloxanes with certain functional groups, by themselves or as carriers of active chemical substances, have a variety of advantages over purely organic or inorganic polymers. Such systems include, for example, ion exchangers, heterogeneous complex catalysts or immobilized enzymes. Inorganic polymers, e.g., silica gel or aluminum oxide, unlike organic polymers, possess certain advantages such as providing a stable, rigid structure; a high resistance to temperature and aging; inability to swell and insolubility in organic solvents; as well as the ready accessibility of functional groups anchored thereon. Their disadvantages, however, reside in providing only a limited capacity for functionalization and the relatively weak anchoring of the functional groups in the solid polymer.

Attempts have been made in the past to overcome some of these disadvantages, for example, by providing silica gel with a coating of polystyrene (H. Arai, T. Kaneko, and T. Kunugi, Chemistry Letters 1975, 265) in order thereby to combine the good properties of the inorganic carrier with those of the organic substance. However, this approach has been successful only in a very limited number of cases.

In comparison, use of suitable organopolysiloxanes, as disclosed, for example, in European patent application No. 0 072 435, is advantageous, as indicated therein. In that document, one comes much closer to the goal of creating an optimal carrier material. However, an important prerequisite for this is primarily to develop and provide suitable monomer precursors. This is the principal objective of the present invention.

This primary objective is achieved according to the invention by the synthesis of novel phenylene group-containing organosilanes, which can be readily converted into the corresponding organopolysiloxanes. Both the organosilanes and the organopolysiloxanes synthesized therefrom can be functionalized by known methods of organic synthesis to make them conform to a desired application.

The invention has as its object to provide phenylene group-containing organosilanes, which are characterized by the general formula:

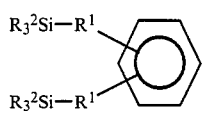 (1)

where in each case all three possible isomers in relation to the position of the $R_3^2Si-R^1$ substituents on the phenylene group can be present concurrently, whereby the bridge groups $R^1$ represent the groups $-CH_2-CH_2-$ or $CH_3-CH<$ and can be identical or different, and the substituents $R^2$ represent chloride or a linear or branched alkoxy group with 1 to 3 carbon atoms and can be identical or different.

The ratio of the three existing isomers relative to the position of the $R_3^2Si-R^1$ substituents on the phenylene groups can be adjusted at will. Both the ortho- as well as the meta- or the para-isomers may predominate. Likewise, only two or even only one isomer of the possible three can be provided.

It has been found that the type and composition of the isomers have no effect on the polycondensation characteristic and only a minor, or no effect at all on the properties of the phenylene group-containing organopolysiloxanes obtainable therefrom.

Further objects of the invention include two processes for the preparation of the new phenylene group-containing organosilanes. The first process is characterized by the reaction in the presence of a suitable hydrosilylation catalyst of a doubly unsaturated compound of the formula:

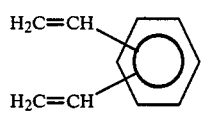 (2)

in which all three possible isomers in relation to the position of the $H_2C=CH$ substituents on the phenylene group can be present concurrently, at a temperature of $-78°$ to $200°$ C. and under a pressure corresponding of the sum of partial pressures of the components of the reaction mixture at the specific temperature, with or without the use of a solvent, and optionally, in the presence of a compound of the formula:

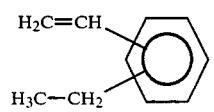 (3)

where all three possible isomers in relation to the position of the $H_2C=CH$ substituent and $H_3C-CH_2$ substituent on the phenylene group can be present concurrently, with stoichiometric or excess amounts, relative to the vinyl groups present, of trichlorosilane or trialkoxysilane of the formula:

 (4)

$$HSiR_3^2$$

in which $R^2$ represents a linear or branched alkoxy residue with 1-3 carbon atoms, and by the purification of the product, optionally by distillation, preferably under vacuum.

The product obtained in the reaction, in the crude state or after purification, can be subsequently utilized for further uses.

The use of a solvent during the addition of trichlorosilane or trialkoxysilane to divinylbenzene is not necessary. If desired, a solvent can be used. In principle, all solvents that do not react with trichlorosilane or trialkoxysilanes are suitable; i.e. solvents that are inert under the conditions of the reaction. Thus, for example, saturated hydrocarbons or aromatic compounds such as, for example, toluene or chlorinated compounds, for example, CCl$_4$, CHCl$_3$, etc. may be used.

The compound of formula (3) may be present in the technical raw material. It has no deleterious effect because the chlorosilane byproducts arising during the hydrosilylation, and these are mainly compounds of the formula:

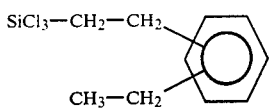

can be readily separated immediately or after esterification of the chlorosilane group by distillation and passed on for appropriate use.

Suitable hydrosilylation catalyts are platinum compounds or elemental platinum on a carrier. Hexachloroplatinic acid or platinum on carbon is especially preferred. Many such catalysts are known in the art and any suitable one may be used herein.

In general, products in which the silyl groups are in the terminal position are primarily formed in the hydrosilylation reaction. The specific distribution of products depends above all on the catalyst employed and on the reaction temperature used. As a general rule, low reaction temperatures favor the formation of the terminal silyl compound. Hexachloroplatinic acid or the combination thereof with PPh$_3$, for example, exhibits high selectivity (up to 90% and higher). However, although the product with terminal silyl groups is preferred, a proportion of up to 20-30% of products with internal silyl groups does not have deleterious effect on the designated application of the silanes of the invention.

The organosilanes of the invention according to formula (1), in which the substituents R$^2$ represent a linear or branched alkoxy group with 1-3 carbon atoms, can also be obtained by esterification of the novel compounds:

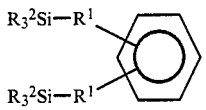

in which R$^2$ represents chloride, with linear or branched alcohols with 1-3 carbon atoms. This esterification can occur immediately after the hydrosilylation reaction without preliminary purification by distillation of the hydrosilylation product. It is needless to say that, alternatively, this may be preceded by a purification.

The esterification reaction itself proceeds such that compounds of the formula:

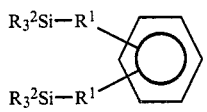

in which R$^2$ represents chloride, are reacted with stoichiometric or excess amounts of a linear or branched alcohol with 1-3 carbon atoms at temperatures of −20° to 200° C. until the total, or nearly total; i.e. essentially total, liberation of the theoretically possible amount of hydrogen chloride gas takes place and any excess alcohol is removed from the product and/or the product is purified by distillation, preferably in vacuum.

This so-called alcoholysis of phenylene group-containing organosilanes of the formula:

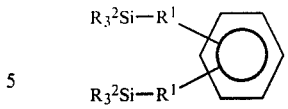

occurs similarly to the known alcoholysis of other chlorosilanes. In this case, a relatively large amount of oligomers is formed in every case, but these oligomers, and this also supplies to the novel silanes of formula (1), can be used precisely as the corresponding monomers in most applications. Purification by distillation of phenylene group-containing organosilanes after the esterification reaction is unnecessary, if the products serve as raw materials, for example, for corresponding polysiloxanes. If desired, a dry inert gas can also be passed through the reaction mixture during the alcoholysis to drive the evolving hydrogen chloride gas out as rapidly as possible. It goes without saying that bromosilanes and iodosilanes can be used instead of chlorosilanes.

The following examples are illustrative of the present invention.

EXAMPLE 1

1212 g of a mixture consisting of up to about 75% by weight of divinylbenzene with an ortho:meta:para ratio of 12:65:23 and up to about 25% by weight of ethyl vinylbenzene was added to 143.5 mg of H$_2$PtCl$_6$.6H$_2$O dissolved in 20 ml of isopropanol, and to 72.6 mg of PPh$_3$ dissolved in 20 ml of CH$_2$Cl$_2$. To this mixture was added dropwise 2200 g of trichlorosilane over 2.0 hours in a 4-liter three-neck flask equipped with a KPG stirrer, internal thermometer, rapid condenser, and dropping funnel. In the process, the internal temperature was maintained at 70°-75° C. by constant cooling of the reaction flask with ice.

After an hour of subsequent reaction at the same temperature, the reaction flask was provided with a 60-cm Vigreux column and the flask content was fractionated under vacuum. In addition to a relatively low boiling first fraction, which still contained some unreacted vinyl group-containing starting material, 620 g of a fraction boiling at 102°-105° C./0.2 mbar was isolated, whereby, according to NMR spectroscopic analysis and the elemental analysis, up to over 90% was the isomer compound:

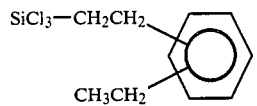

Next, 2480 g of the desired product isomer mixture was obtained at a temperature of 155°-163° C. and under a pressure of 0.1 mbar in the form of a colorless liquid with a density d$_4^{20}$=1.34 g/cm$^3$. According to the NMR spectrum, the terminal addition compounds:

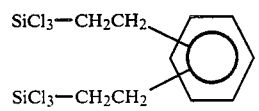

comprised up to about 90% of this.

The isomer distribution corresponded to the isomer distribution of the starting material. The internal addition compounds of the formula:

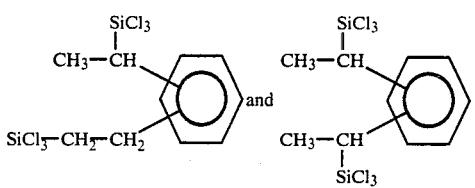

comprised up to about 10%.

| Elemental analyses: | % C | % H | % Si | % Cl |
|---|---|---|---|---|
| Theoretical: | 29.95 | 3.02 | 14.00 | 53.03 |
| Found: | 29.40 | 3.15 | 13.79 | 53.20 |

The yield of the desired product mixture could have been increased further, if the amount of $HSiCl_3$ employed had been increased.

EXAMPLE 2

1000 g of the product prepared according to Example 1 and comprising up to about 90% of the ortho-, meta-, and para-isomer mixture (isomer distribution: 12% by weight/65% by weight/23% by weight) of the compound:

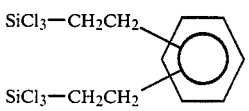

and up to about 10% of the compounds:

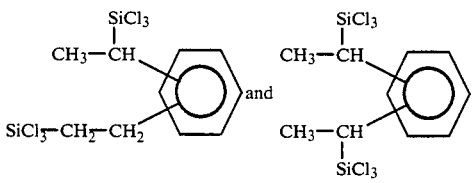

(distribution of substances by weight 2:1) with the identical isomer distribution in each case, were charged to a 4-liter four-neck flask equipped with an internal thermometer, KPG stirrer, rapid reflux condenser (cooling brine: −20° C.), and dropping funnel.

The gas outlet of the rapid reflux condenser was connected to a vessel filled with 2.5 liters of 40% sodium hydroxide solution. After the starting material was heated to 40° C. with vigorous stirring, 723.6 g of ethanol was added dropwise over 2.5 hours. After the addition of ethanol ended, the dropping funnel was removed and replaced by a gas inlet tube through which dried nitrogen gas was injected into the reaction mixture. At the same time, the mixture was heated to reflux temperature over 1.5 hours. The mixture was further stirred for another 4 hours at reflux until almost no further HCl evolution could be determined. Then, the formed product was fractionated over a 40-cm Vigreux column. Obtained as the main fraction at a transition temperature of 170°–173° C./0.05 mbar was 1011 g (88.4% of the theoretical) of the desired product with the o-, m-, and p-isomers:

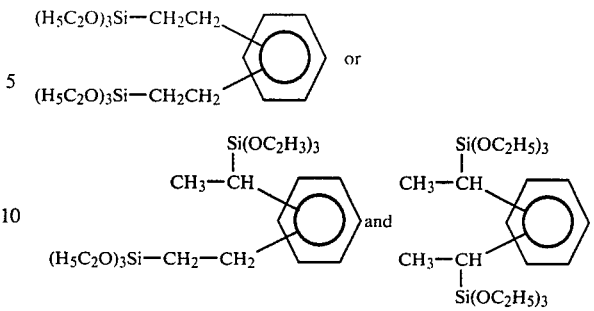

(corresponding to distribution of amounts by weight given for the starting material) ($d_4^{20} = 0.99$ g/cm$^3$).

| Elemental analyses: | % C | % H | % Si |
|---|---|---|---|
| Theoretical: | 57.60 | 9.23 | 12.24 |
| Found: | 56.48 | 9.20 | 11.86 |

As was demonstrated by NMR spectroscopy, the bottoms residue remaining after distillation consisted of the corresponding oligomer products, which were formed during this alcoholysis as in most esterification reactions of halosilanes.

EXAMPLE 3

1000 g of the product according to Example 1 was esterified with methanol as in Example 2. With the use of similar equipment, 505 g of methanol was charged to the starting material at room temperature over 4 hours. Then, the mixture was heated over 2 hours to reflux temperature and stirred for another 3 hours at reflux. After withdrawal of excess methanol, 918.2 g of the desired isomer products:

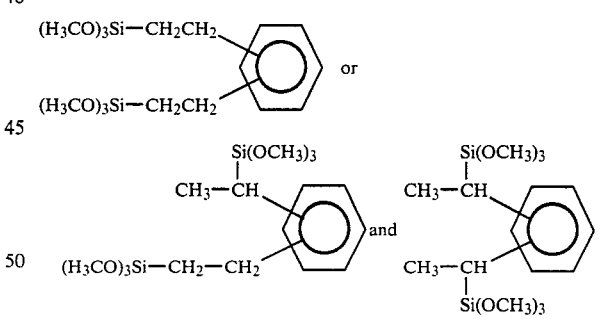

was obtained at a temperature of 100° C./20 mbar. Because a higher proportion of oligomer compounds is generally formed during the methanolysis of chlorosilanes than in ethanolysis, a yield-reducing distillation was dispensed with and the product was immediately subjected to further processing. The product was analyzed only by NMR spectroscopy and subjected to elemental analysis. The NMR spectrum corroborated the expected composition.

| Elemental analyses: | % C | % H | % Si | % Cl |
|---|---|---|---|---|
| Theoretical: | 51.30 | 8.07 | 15.00 | 0 |
| Found: | 49.97 | 7.86 | 14.72 | 1.0 |

EXAMPLE 4

500 g of a mixture comprising up to about 92% of divinylbenzene with an ortho:meta:para ratio of 20:55:25 and up to about 8% ethyl vinylbenzene was added to 50 mg of $H_2PtCl_6 \cdot 6H_2O$, dissolved in 10 ml of isopropanol. As in Example 1, 1250 g of $HSi(OC_2H_5)_3$ was added dropwise to this mixture at 80° C. over 2 hours. After 4 hours of subsequent reaction at the same temperature, the product was fractionated under vacuum. 1507.4 g (93.0% of the theoretical) of the desired product was obtained, which was composed of up to about 85% of the terminal addition compounds and up to about 15% of the internal addition compounds in the predetermined isomer distribution in each case.

Further variations and modifications of the present invention will be apparent to those skilled in the art from the foregoing description and which are intended to be encompassed by the claims appended hereto.

The German priority documents P No. 35 18 878.2 is relied on and incorporated herein by reference.

We claim:

1. A phenylene group-containing organosilane represented by the formula:

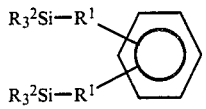
(1)

where in each case all three possible isomers in relation to the position of the $R_3Si$—$R^1$ substituents on the phenylene group can be present concurrently, whereby the bridge groups $R^1$ represents —$CH_2CH_2$— or $CH_3CH<$ and may be identical or different, and the substituent $R^2$ represents chloride or a linear or branched alkoxy group with 1 to 3 carbon atoms and may be identical or different.

2. A process for the preparation of the compounds set forth in claim 1, comprising reacting a doubly unsaturated compound represented by the formula:

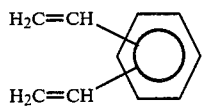
(2)

in which all three possible isomers in relation to the position of the $CH_2$=$CH$ substituents on the phenylene group can be present concurrently, in the presence of a hydrosilylation catalyst at a temperature of −78° to 200° C. and under a pressure corresponding to the sum of the partial pressures of the components of the reaction mixture at the specific temperature, with a stoichiometric or excess amount, in relation to the vinyl groups present, of trichlorosilane or trialkoxysilane of the formula:

(4)

in which $R^2$ represents a linear or branched alkoxy group with 1-3 carbon atoms.

3. The process according to claim 2 further comprising carrying out the reaction in the presence of a compound of the formula:

(3)

in which all three possible isomers in relation to the position of the $H_2C$=$CH<$ substituent and $H_3C$—$CH_2$ substituent on the phenylene group can be present concurrently.

4. The process according to claim 2 further comprising recovering the product.

5. The process according to claim 4 further comprising purifying the product by distillation.

6. The process according to claim 5 wherein the distillation is under vacuum.

7. The process for the preparation of the compounds set forth in claim 1, in which $R^3$ in formula (1) represents a linear or branched alkoxy group with 1-3 carbon atoms, and comprising reacting a compound:

(1)

in which $R^2$ is chloride, with stoichiometric or excess amounts of a linear or branched alcohol with 1-3 carbon atoms, at temperatures of −20° C. to 200° C. until at least essentially total liberation of the theoretically possible amount of hydrogen chloride gas occurs, and any excess alcohol is removed from the product.

8. The process according to claim 7 wherein the product is purified by distillation.

9. The process according to claim 8 wherein the distillation is in vacuum.

* * * * *